(12) United States Patent
Bellorini et al.

(10) Patent No.: US 9,066,858 B2
(45) Date of Patent: Jun. 30, 2015

(54) PHARMACEUTICAL COMPOSITION FOR THE SUBLINGUAL ADMINISTRATION OF PROGESTERONE, AND METHOD FOR ITS PREPARATION

(75) Inventors: Lorenzo Bellorini, Comerio (IT); Luca Nocelli, Luino (IT); Giorgio Zoppetti, Milan (IT)

(73) Assignee: ALTERGON S.A., Lugano (CH)

( * ) Notice: Subject to any disclaimer, the term of this patent is extended or adjusted under 35 U.S.C. 154(b) by 760 days.

(21) Appl. No.: 12/734,078

(22) PCT Filed: Oct. 10, 2008

(86) PCT No.: PCT/EP2008/063595
§ 371 (c)(1),
(2), (4) Date: Apr. 7, 2010

(87) PCT Pub. No.: WO2009/047321
PCT Pub. Date: Apr. 16, 2009

(65) Prior Publication Data
US 2010/0240631 A1   Sep. 23, 2010

(30) Foreign Application Priority Data

Oct. 10, 2007 (IT) .............................. MI2007A1971

(51) Int. Cl.

| | |
|---|---|
| A61K 31/57 | (2006.01) |
| A61P 5/24 | (2006.01) |
| A61P 15/18 | (2006.01) |
| A61K 9/00 | (2006.01) |
| A61K 9/46 | (2006.01) |
| A61K 31/00 | (2006.01) |
| A61K 47/48 | (2006.01) |
| B82Y 5/00 | (2011.01) |
| C08B 37/16 | (2006.01) |
| C08L 5/16 | (2006.01) |
| A61K 9/20 | (2006.01) |

(52) U.S. Cl.
CPC ............... *A61K 9/006* (2013.01); *A61K 9/0007* (2013.01); *A61K 9/0056* (2013.01); *A61K 9/2009* (2013.01); *A61K 9/205* (2013.01); *A61K 31/00* (2013.01); *A61K 47/48969* (2013.01); *B82Y 5/00* (2013.01); *C08B 37/0015* (2013.01); *C08L 5/16* (2013.01)

(58) Field of Classification Search
USPC ........................................................ 514/177
See application file for complete search history.

(56) References Cited

U.S. PATENT DOCUMENTS

| | | | |
|---|---|---|---|
| 4,596,795 A | 6/1986 | Pitha | |
| 2004/0115258 A1* | 6/2004 | Stroppolo et al. | ............ 424/465 |

OTHER PUBLICATIONS

International Search Report of PCT/EP2008/063595 dated Jul. 5, 2009.

* cited by examiner

*Primary Examiner* — Kathrien Cruz
(74) *Attorney, Agent, or Firm* — Novak Druce Connolly Bove + Quigg LLP

(57) ABSTRACT

A pharmaceutical composition is described for the sublingual administration of progesterone in the form of a rapidly-disintegrating tablet, which is capable of promoting a greater bioavailability of the progesterone; a method for preparing said pharmaceutical composition is also described.

1 Claim, 1 Drawing Sheet

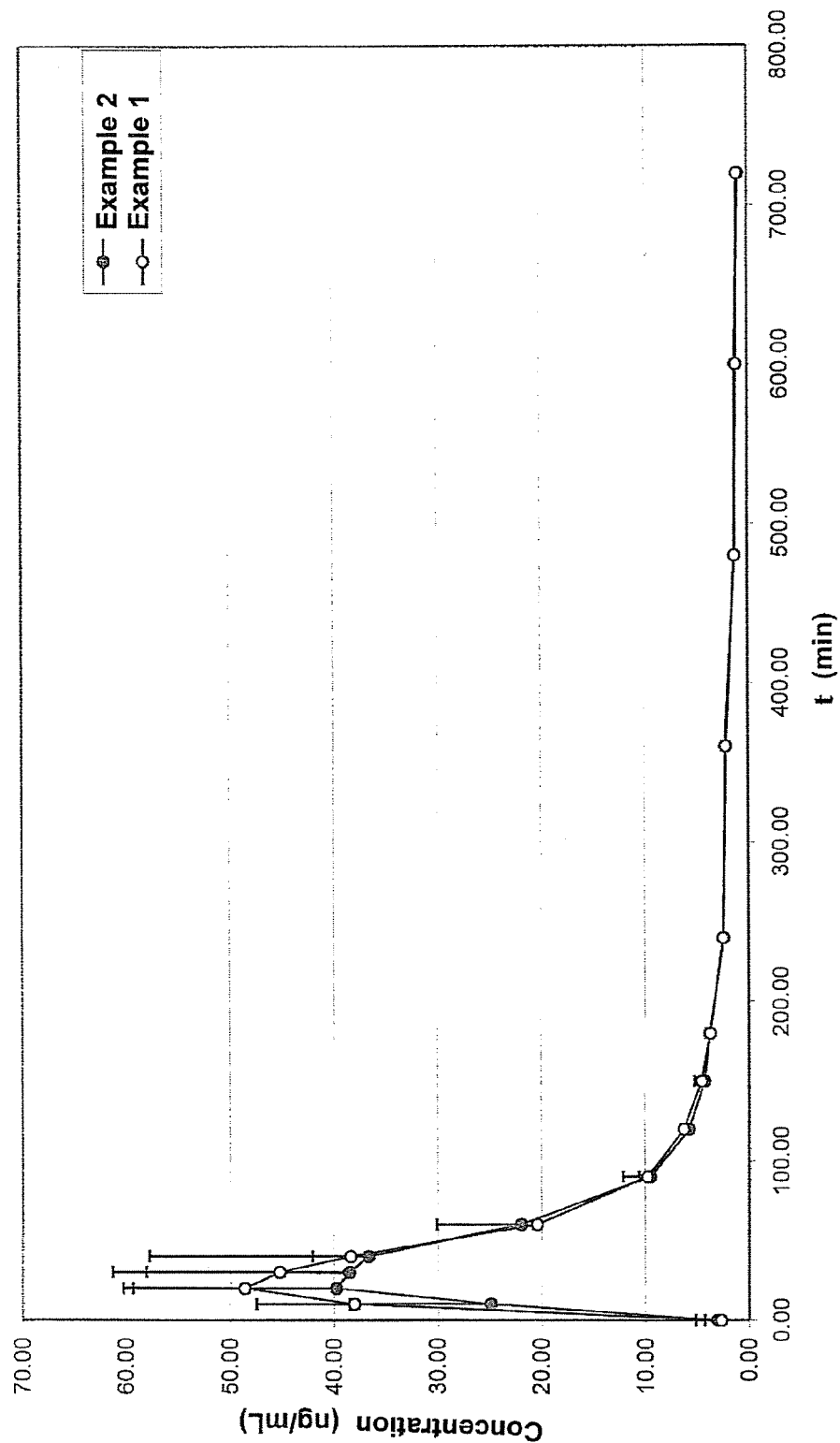

PHARMACEUTICAL COMPOSITION FOR THE SUBLINGUAL ADMINISTRATION OF PROGESTERONE, AND METHOD FOR ITS PREPARATION

CROSS REFERENCE TO RELATED APPLICATION

This application is a §371 of PCT/EP2008/063595, filed Oct. 10, 2008, which claims priority from Italian Application No. MI2007A001971, filed Oct. 10, 2007, all of which are incorporated herein by reference.

FIELD OF THE INVENTION

The present invention refers to a new pharmaceutical composition for the sublingual administration of progesterone, and to a method for its preparation.

STATE OF THE ART

Progesterone is a steroid hormone that is naturally secreted by the ovaries in the second half of the menstrual cycle of fertile women of reproductive age; it is used for therapeutic purposes, e.g. in hormone replacement therapy for menopausal women, in oral contraceptives and for regulating the menstrual cycle.

Various methods for administering progesterone are known, from the parenteral to the vaginal, to the oral, the last of these being by far the most readily acceptable and comfortable for the patients, especially if they have to undergo lengthy periods of treatment.

The therapeutic efficacy of progesterone is severely reduced when it is administered orally, however, due to a more limited bioavailability deriving from its solubility in water and its rapid degradation by the liver; these two factors contribute to a very poor absorption of the active ingredient in the gastrointestinal tract.

To overcome these problems, it has been suggested that progesterone be administered via absorption in the oral cavity, where it is less affected by a rapid metabolism in the liver than when it is absorbed in the gastrointestinal tract. Said mode of administration generally gives rise to only modest haematic levels of progesterone unless it is administered in the form of its water-soluble derivative. The U.S. Pat. No. 4,596,795, for instance, describes a formulation in tablets for administering progesterone buccally or sublingually in the oral cavity, in which the progesterone is combined with specific beta-cyclodextrins. In fact, when combined with these compounds, progesterone forms inclusion complexes that are soluble in an aqueous environment, thereby favouring its bioavailability.

In the case of its sublingual administration, this patent indicates the need for the tablet to disintegrate, which takes several minutes.

SUMMARY

According to the present invention, it has now surprisingly been discovered that adding certain excipients to a composition comprising progesterone and a cyclodextrin gives rise to a powder that can be compressed to obtain a tablet which is sufficiently compact for packaging but that nonetheless disintegrates rapidly when administered sublingually, and that said rapidly-disintegrating tablet is able, when administered sublingually, to promote a greater bioavailability of the progesterone than a tablet lacking said excipients.

By rapid disintegration, we mean a time preferably lasting no more than two minutes.

The subject of the present invention is therefore a pharmaceutical composition for the sublingual administration of progesterone associated with a cyclodextrin, characterised in that it is in the form of a rapidly-disintegrating tablet comprising excipients capable of releasing $CO_2$ in the sublingual site.

For said purpose it preferably comprises a bicarbonate, such as sodium bicarbonate, and a suitable acid, such as citric acid.

According to the present invention, by progesterone associated or combined with a cyclodextrin, we mean a complexing derivative such as those described in U.S. Pat. No. 4,596,795.

A further object or the invention is a method used to prepare the aforesaid pharmaceutical composition, which can be achieved by means of the following stages:
a) sieving the excipients and the raw material;
b) mixing;
c) compressing the mixture to produce said finished tablet.

Characteristics and advantages of the pharmaceutical composition according to the present invention are illustrated in more detail in the description that follows.

BRIEF DESCRIPTION OF THE DRAWINGS

FIG. 1 shows a diagram comparing the concentration (ng/ml) of progesterone in the serum against the time after the sublingual administration of 20 mg of active ingredient using the tablets prepared as in example 1 (invention) and example 2 (reference).

DETAILED DESCRIPTION OF THE INVENTION

Reference is made below to the non-limiting case in which said excipients capable of releasing $CO_2$ in the sublingual site are citric acid and sodium bicarbonate.

The quantity of citric acid contained in the composition of the invention is, for instance, comprised between 5 and 20% w/w of the total weight of the composition, and preferably amounts to 10% w/w.

The quantity of bicarbonate contained in the composition of the invention is, for instance, comprised between 5 and 20% w/w of the total weight of the composition, and preferably amounts to 12% w/w.

The bicarbonate contained in the composition of the invention is preferably sodium bicarbonate.

According to a preferred embodiment of the invention, the molar ratio of the progesterone to the cyclodextrin is between 1 and 2.

A cyclodextrin suitable for use in the present composition may be, for instance, either β-cyclodextrin or 2-hydroxypropyl-β-cyclodextrin; the composition of the invention preferably contains 2-hydroxypropyl-β-cyclodextrin.

The quantity of cyclodextrin contained in the composition shall preferably be between 27 and 40% w/w of the total weight of the composition.

In addition to the active ingredient (progesterone), a cyclodextrin and the pair of excipients with an effervescent action (citric acid and bicarbonate), the pharmaceutical compositions according to the invention may comprise further pharmacologically suitable excipients chosen from among those conventionally used in pharmaceutical preparations to obtain a composition in the form of a rapidly-disintegrating tablet.

The present pharmaceutical composition in tablet form, though it is hard enough to enable it to retain its shape and remain intact so that the product can be packaged and preserved, when it is placed under the tongue it nonetheless disintegrates rapidly, becoming completely disintegrated within a time generally between 60 and 120 seconds.

Moreover, pharmacokinetic studies (described in more detail in Example 3) have demonstrated an approximately 30% increase in the bioavailability of the progesterone in the compositions according to the present invention by comparison with similar compositions for sublingual administration that lack the pair of effervescent excipients, such as citric acid and sodium bicarbonate.

The compositions according to the invention can be prepared to contain various unit doses of progesterone, for instance, between 5 and 30 mg of progesterone, and preferably amounting to 20 mg.

The following examples are given as a non-limiting illustration of the present invention.

EXAMPLE OF THE PREPARATION METHOD 1

Formulation:
1) hydroxypropyl-β-cyclodextrin, Kleptose (HPBCD) batch E0033 kg 13.5
2) progesterone micron. batch L00025494 kg 1.35
3) distilled water of 13.06.05 kg 55.4625

Method For Preparing the Solution to Lyophilize:
1) kg 42.2625 of distilled water are transferred to a dissolver (A) with a capacity of 200 L;
2) the first semiprocessed product is prepared in a separate stainless steel container (B);
distilled water kg 6.6
hydroxypropyl-β-cyclodextrin, Kleptose (HPBCD) kg 6.75
and agitated for 20 minutes at ambient temperature;
the deaerated solution appears clear and contains no residues;
3) progesterone micron. kg 0.675 is added to the solution prepared according to step 2;
the mixture is agitated for 45 minutes at ambient temperature;
the resulting solution is transferred to a dissolver prepared according to step 1;
4) the second semiprocessed product is prepared according to steps 2 and 3 in a stainless steel container (B) and transferred to a dissolver (A) prepared according to steps 1 and 3;
5) the final solution is mixed for 10 minutes in a 200 L dissolver;
the resulting solution is clear and contains no air bubbles;
approximately 40 mL of solution are drawn off for analyses;
the solution is placed in the lyophilizer;
6) the solution is forced through a 0.46 μm column filter under a pressure of 2 bar of anhydrous air;
7) the solution is placed on disposable high-density polyethylene mats in a continuous flow (16—maintaining a bulk thickness of 1 cm);
8) the product is lyophilized;
9) the resulting bulk product is ground in an oscillating granulator and passed through a 1 mm sieve;
13.9 kg of end product are obtained;
10) the product is placed in three aluminium containers, which are then sealed.

The resulting powder has the following characteristics:
Bulk humidity when unloaded from the mats 0.9%.
Humidity after grinding 1.5%.
Bulk density after pouring=0.26 g/ml
Bulk density after compacting=0.32 g/ml
Particle size distribution:
95% between 50 and 800 μm
mean=260 μm

EXAMPLE 1

Method for Preparing Tablets for the Sublingual Administration of Progesterone According to the Invention The single components are separately weighed and labelled as follows:

|   |   | Weight in g |
|---|---|---|
| 1 | Progesterone complex (as described in the example preparation method 1) | 1507 |
| 2 | Polyvinylpyrrolidone CL | 253.45 |
| 3 | Citric acid anhydrous powder | 445.25 |
| 4 | Sodium bicarbonate powder | 548 |
| 5 | Calcium silicate | 616.5 |
| 6 | Sorbitol | 787.75 |
| 7 | Sodium stearyl fumarate | 34.25 |
| 8 | E951 (Aspartame) | 137 |
| 9 | Flavouring | 226.05 |
|   | TOTAL | 4555.25 |

Ingredients 1), 2), 3), 4), 5), 6) and 9) are premixed and sieved through a wire sieve with 1 mm net mesh holes and loaded in a mixer.

Component 8) is separately sieved through a 0.5 mm wire sieve and loaded in the mixer.

The ingredients are mixed for 25 minutes at a speed of 20 rpm/60".

Component 9) is sieved through a 0.2 mm wire sieve and loaded in the mixer.

Mixing proceeds with the other ingredients for 5 minutes at a speed of 20 rpm/60".

The powder is unloaded and compressed with a round punch 16 mm in diameter, setting a mean weight of 665 mg±3% and a mean hardness of 35 N±3N.

The tablets are blister-packed in a suitable format and placed in cardboard boxes.

The resulting tablets have the following characteristics:
mean weight=660.4, mean titre=103.1% d.d., hardness=33N and disintegration time=100 sec.

EXAMPLE 2

Comparison

Method for Preparing Tablets for the Sublingual Administration of Progesterone without Citric Acid and Bicarbonate The single components are separately weighed and labelled as follows:

|   |   | Weight in g |
|---|---|---|
| 1 | Progesterone complex (as described in the example preparation method 1) | 44 |
| 2 | Polyvinylpyrrolidone CL | 7.4 |
| 3 | Calcium silicate | 18 |
| 4 | Sorbitol | 52 |
| 5 | Sodium stearyl fumarate | 1 |
| 6 | E951 (Aspartame) | 4 |
| 7 | Flavouring | 6.6 |
|   | TOTAL | 133 |

Ingredients 1), 2), 3), 4) and 7) are premixed and sieved through a wire sieve with 1 mm net mesh holes and loaded in a mixer.

Component 6) is separately sieved through a 0.5 mm wire sieve and loaded in the mixer.

The ingredients are mixed for 25 minutes at a speed of 20 rpm/60".

Component 5) is sieved through a 0.2 mm wire sieve and loaded in the mixer.

Mixing proceeds with the other ingredients for 5 minutes at a speed of 20 rpm/60".

The powder is unloaded and compressed with a round punch 16 mm in diameter, setting a mean weight of 665 mg±3% and a mean hardness of 35 N±3N.

The tablets are blister-packed in a suitable format and placed in cardboard boxes.

The resulting tablets have the following characteristics: mean weight=664, mean titre=101.1% d.d., hardness=32N and disintegration time=90 sec.

EXAMPLE 3

Pharmacokinetic Study

A preliminary pharmacokinetic study was conducted to compare the administration of tablets according to the invention, obtained as described in example 1, with those prepared for comparison as described in example 2.

The diagram in the attached drawing (FIG. 1) compares the concentration (ng/ml) of progesterone in the serum against the time after the sublingual administration of 20 mg of active ingredient using the tablets prepared as in example 1 (invention) and example 2 (reference).

The two curves plotted in the diagram represent the mean (+SD) of the values obtained in three subjects treated as described above.

Clearly, the curve relating to example 1 shows an approximately 30% greater mean bioavailability than the curve relating to example 2.

The invention claimed is:

1. A pharmaceutical composition for the sublingual administration of progesterone complexed with a cyclodextrin, in the form of a rapidly-disintegrating tablet having the following composition by weight:

Progesterone complex
with hydroxypropyl-β-cyclodextrin: 33.1%
Polyvinylpyrrolidone CL: 5.6%
Citric acid anhydrous powder: 9.8%
Sodium bicarbonate powder: 12.0%
Calcium silicate: 13.5%
Sorbitol: 17.3%
Sodium stearyl fumarate: 0.8%
Aspartame: 3.0%
Flavouring: 5.0%.

\* \* \* \* \*